United States Patent
Daum et al.

(10) Patent No.: US 6,989,015 B2
(45) Date of Patent: Jan. 24, 2006

(54) NAVIGATION OF MEDICAL INSTRUMENT (75) Inventors: Wolfgang Daum, Groton, MA (US); Axel Winkel, Schwerin (DE)

(73) Assignee: Invivo Germany GmbH (DE)

( * ) Notice: Subject to any disclaimer, the term of this patent is extended or adjusted under 35 U.S.C. 154(b) by 0 days.

(21) Appl. No.: 10/632,685

(22) Filed: Aug. 1, 2003

(65) Prior Publication Data

US 2004/0064148 A1 Apr. 1, 2004

Related U.S. Application Data (63) Continuation of application No. 09/954,725, filed on Sep. 14, 2001, now abandoned.

(51) Int. Cl.
*A61B 19/00* (2006.01)

(52) U.S. Cl. .................................................... 606/130
(58) Field of Classification Search ................ 606/130; 600/378; 607/116, 139
See application file for complete search history.

(56) References Cited

U.S. PATENT DOCUMENTS

| | | | |
|---|---|---|---|
| 4,809,694 A | 3/1989 | Ferrara | |
| 5,201,742 A | 4/1993 | Hasson | |
| 5,515,160 A | 5/1996 | Schulz et al. | |
| 5,517,990 A | 5/1996 | Kalfas et al. | |
| 5,662,111 A | 9/1997 | Cosman | |
| 5,891,034 A | 4/1999 | Bucholz | |
| 5,957,934 A | 9/1999 | Rapoport | |
| 6,117,143 A | 9/2000 | Hynes et al. | |
| 6,173,201 B1 | 1/2001 | Front | |
| 6,235,038 B1 | 5/2001 | Hunter et al. | |
| 6,273,896 B1 * | 8/2001 | Franck et al. | ................ 606/130 |
| 6,282,437 B1 | 8/2001 | Franck et al. | |
| 6,298,262 B1 | 10/2001 | Franck et al. | |
| 6,314,310 B1 | 11/2001 | Ben-Haim et al. | |
| 6,351,662 B1 | 2/2002 | Franck et al. | |
| 6,529,765 B1 | 3/2003 | Franck et al. | |

FOREIGN PATENT DOCUMENTS

| | | |
|---|---|---|
| DE | 197 26 141 A1 | 1/1999 |
| DE | 198 44 767 A1 | 4/2000 |

* cited by examiner

*Primary Examiner*—Ralph A. Lewis
(74) *Attorney, Agent, or Firm*—Saliwanchik, Lloyd & Saliwanchik (57) ABSTRACT

The subject invention pertains to a device for inserting medical instruments into the human body. In a specific embodiment, the subject device can be made from a material which is invisible under Magnetic Resonance Imaging (MRI). The subject device can incorporate three or more MRI compatible marks. The imaging of these three or more markers can allow the determination of the orientation of the device. A virtual image of the device can then be shown in an MRI image.

12 Claims, 11 Drawing Sheets

NAVIGATION OF MEDICAL INSTRUMENT

CROSS REFERENCE TO A RELATED APPLICATION

This application is a continuation of application U.S. Ser. No. 09/954,725; filed Sep. 14, 2001 now abandoned.

BACKGROUND OF THE INVENTION

With the German patent specification DE 198 44 767 A1, a method attaching markers to a medical instrument that are detectable under MRI is already known. The orientation of the instrument within the MRI device can be determined with these points. However, the respective allocation of the measured markers to the instrument markers is impeded due to the similarity of the signal-emitting substance to the instrument material. The non-availability of an instrument fixation to the patient proves to be a further disadvantage. Such fixation could be achieved by use of trocars. FIGS. 2, 3, 4, and 5 show a device ensuring a minimally-invasive approach to the brain through a hole in the top of the skull. Such trocar is already known from patent specification DE 197 26 141 and prevents the risk of the so-called Brain Shift, which signifies the uncontrolled shifting of the brain inside the surrounding skull during an operation. This problem is not limited to the neuro field, but occurs whenever shifting tissue is punctured. The disadvantages of this kind of trocars are the following points:

The adjustment of a navigation system adapting the devices to MRI imaging to such a neuro trocar is difficult.

The neuro trocar is manufactured of titanium alloy, so that it is depicted as a homogenous formation with indistinct rim demarcation in the MR image. A three-dimensional orientation is difficult to assess. This, however, is highly essential, with the neuro trocar, unlike a stereotactic system, having no own reference point as it is fixed to the patient.

The invention presented herein aims to solve these and other problems.

BRIEF SUMMARY OF THE INVENTION

The subject invention pertains to a device for inserting medical instruments into the human body. In a specific embodiment, the subject device can be made from a material which is invisible under Magnetic Resonance Imaging (MRI). The subject device can incorporate three or more MRI compatible markers. The imaging of these three or more markers can allow the determination of the orientation of the device. A virtual image of the device can then be shown in an MRI image.

DETAILED DESCRIPTION OF THE FIGURES

DETAILED DESCRIPTION OF THE INVENTION

The problem of the conventional neuro trocar being not sufficiently identifiably with regard to its orientation within the MRI, as described in patent DE 197 26 141, can be solved by designing a device of a material that is totally invisible under MRI. If then a minimum of three MRI compatible points are marked on it, an exact orientation can be determined by these three points; its position in the MRI procedure can be precisely assessed, and a virtual image of the trocar can be shown in the MRI picture.

Various systems for the technical realization of these points are described below.

Figure 1:
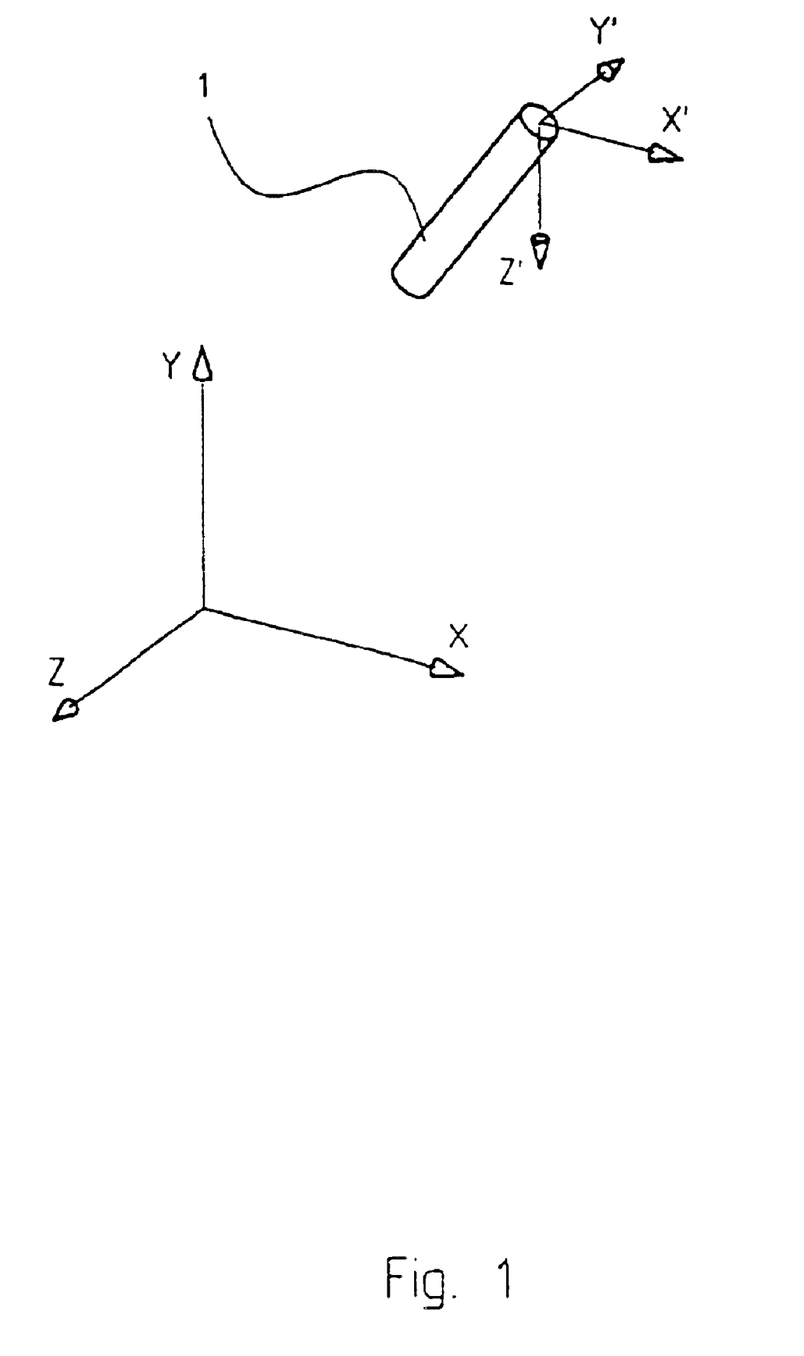
FIG. 1 shows a problem of navigation.

The problem is shown in FIG. 1. The medical instrument 1 with its reactive coordination system x'y'z' shall be determined in its position relative to the patient coordination system xyz.

Figure 4:
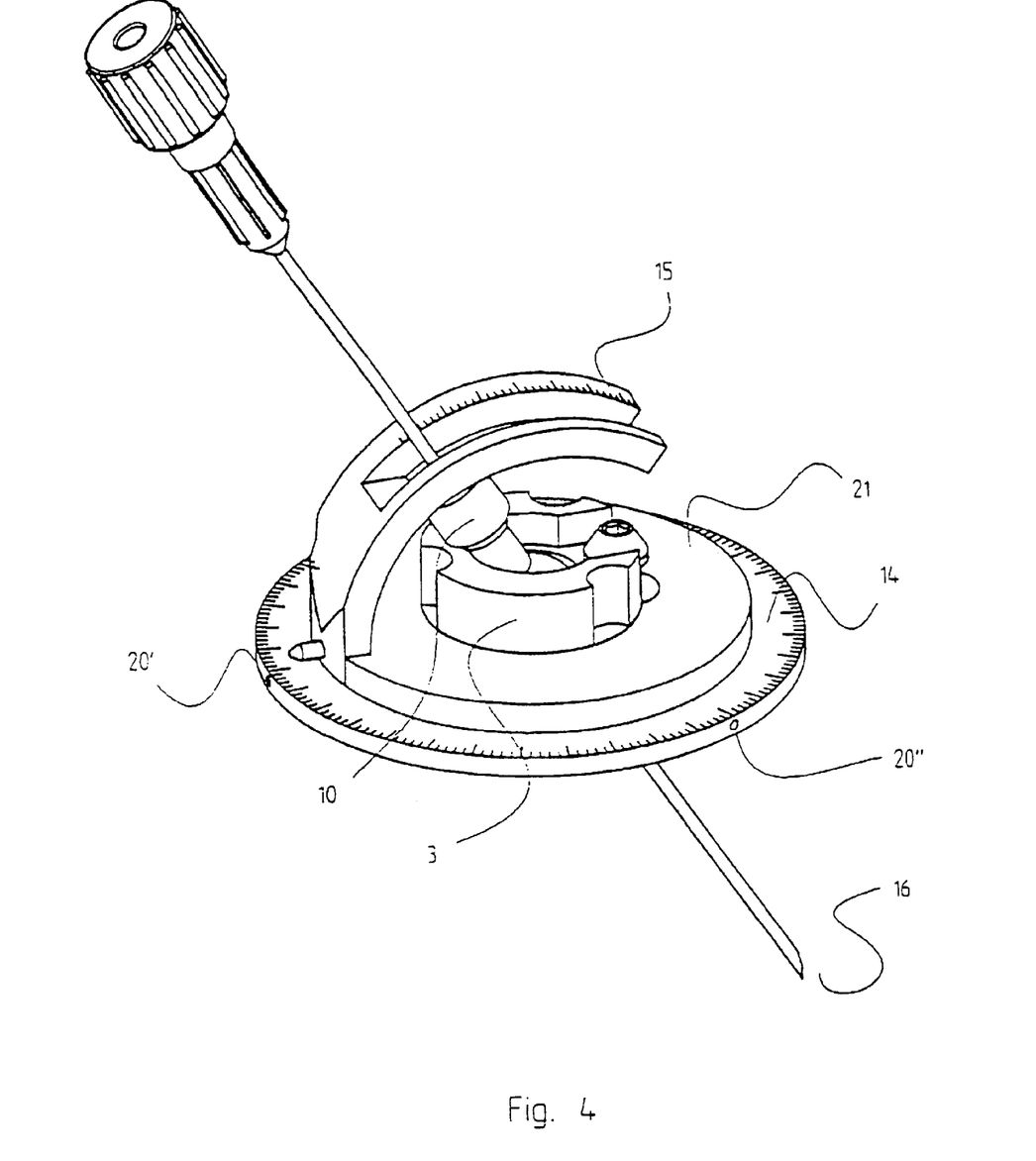
FIG. 4 shows angle measurement between instrument insertion channel and device in accordance with and embodiment of the present invention.

Both the adjustment of the instrument insertion channel 10 and the adjustment of the device 3, which essentially corresponds to the devices 1 and 2, can be correlated to each other by an angle adjustment (see FIG. 4). An angle adjustment for the azimuth angle 14 and an angle adjustment for the zenith angle 1 are possible on the device 3. When the position of the device 3 is known, the position of the instrument insertion channel 10 will also be known automatically. By an automatic pick-off of angular movement not shown in FIG. 4, azimuth and zenith angle could be directly measured and included into the MR image. The MR image could then always adjust to the orientation of the instrument insertion channel 10 so that the operation site 16 will always be optimally in the sight vane in the imaging of the MRI device. In such case, markers according to the principles 20', 20'', and 20''' stated herein could be adapted in the device 3 or in a top for angle measurement 21. Reversedly, it is also possible to measure the angle within the MR image and then to adjust at the device, i.e., the device follows the MR image.

Figure 5:
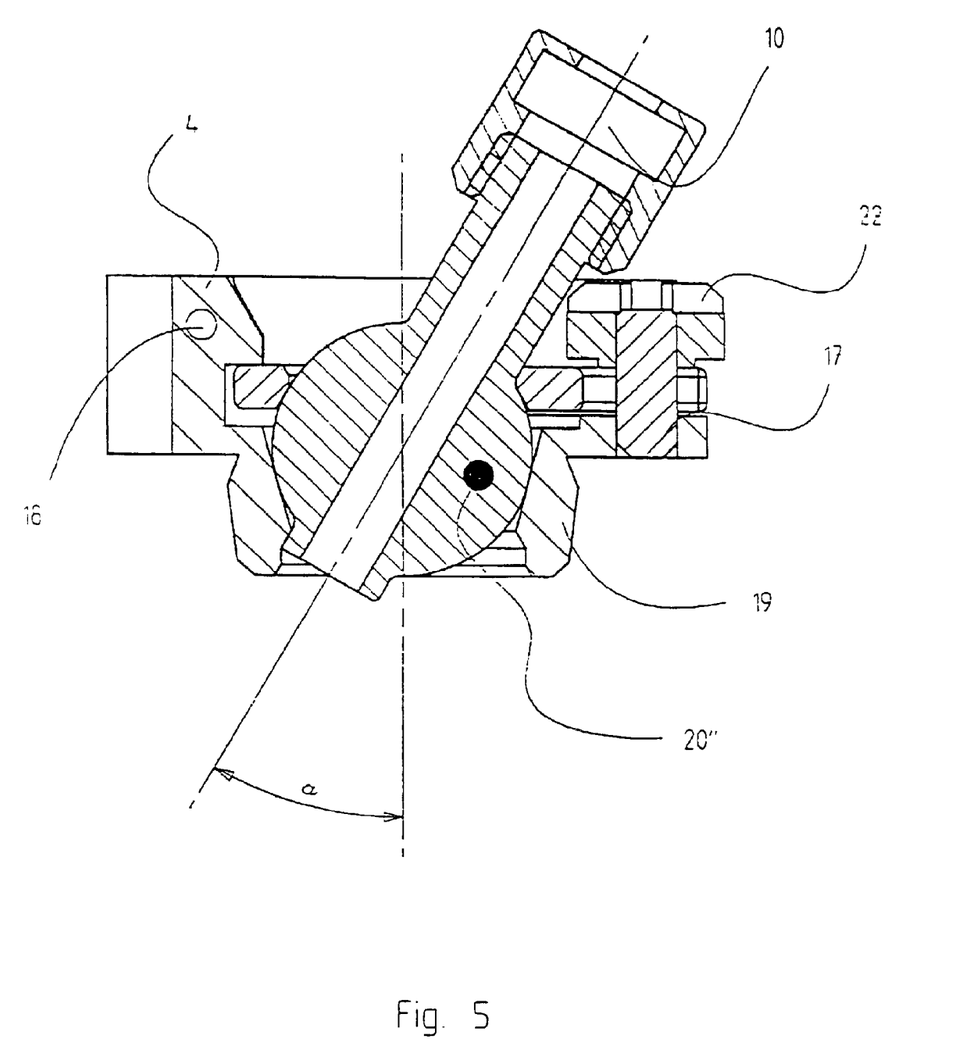
FIG. 5 shows navigation with active and passive material contrast in accordance with and embodiment of the present invention.

The fixation of the instrument insertion channel 10 in a certain position can be achieved by tightening a fixing screw 22 as shown in FIG. 5.

Figure 6:
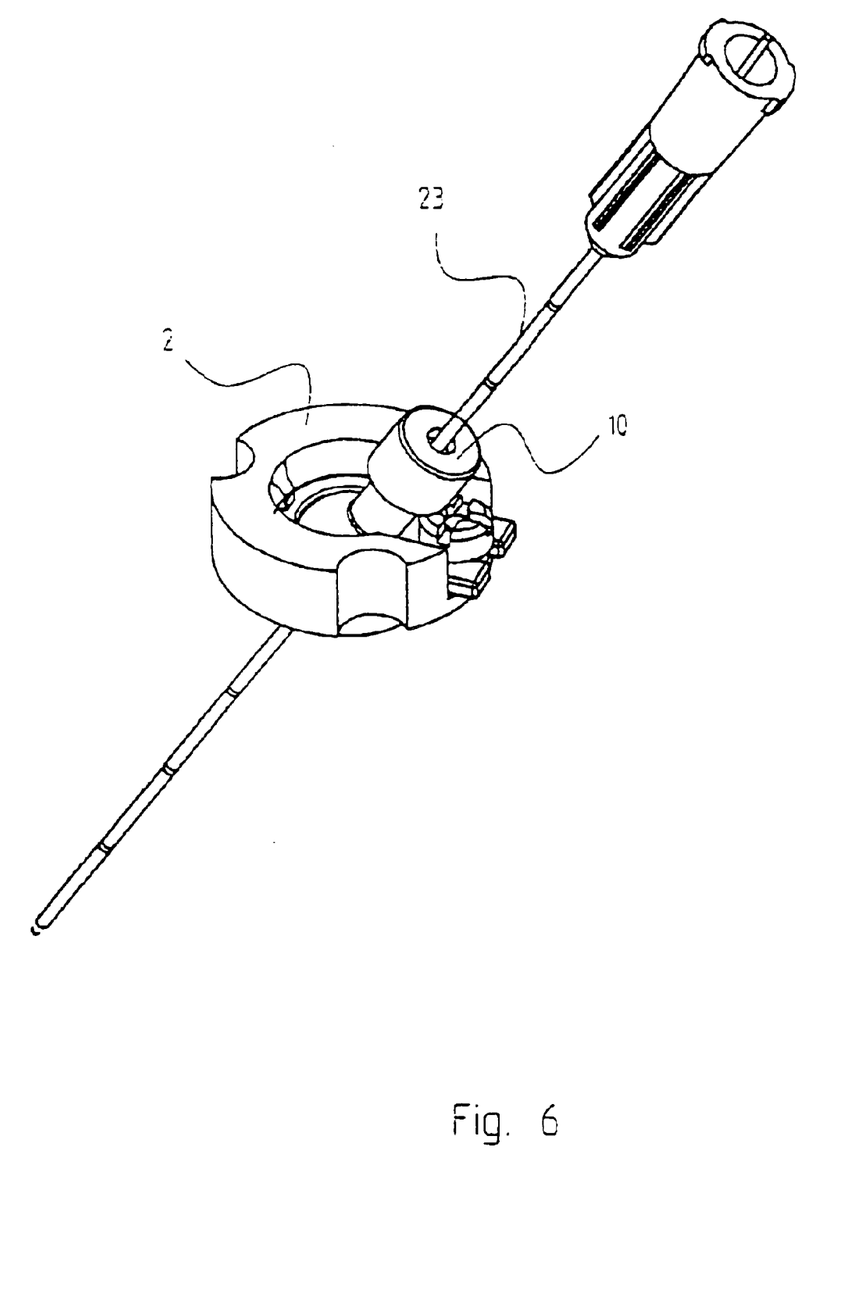
FIG. 6 shows a device with a stabilization channel in accordance with an embodiment of the present invention.
Figure 8:
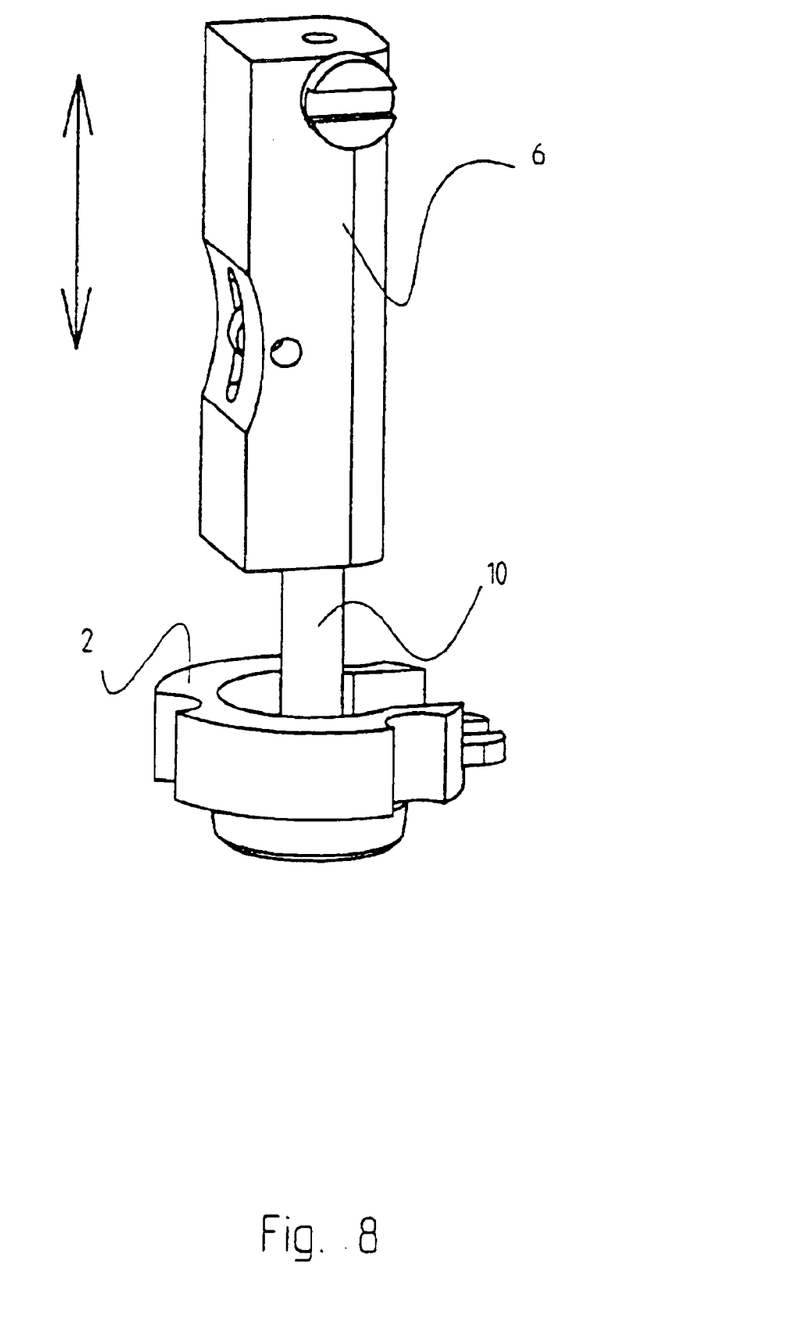
FIG. 8 shows linear propulsion at the instrument insertion channel in accordance with an embodiment of the present invention.
Figure 9A:
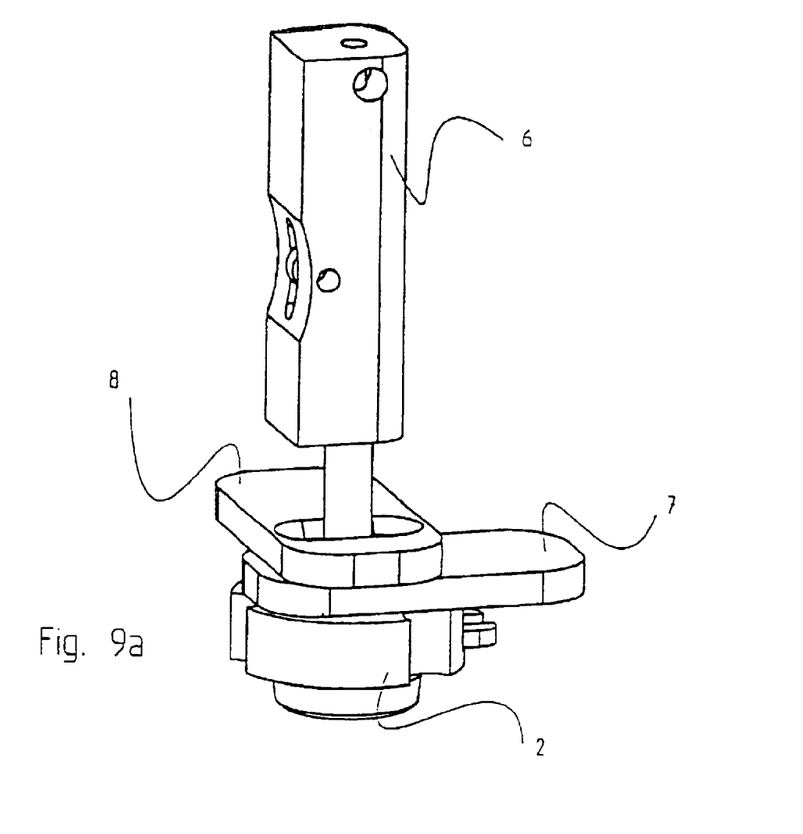
FIG. 9a shows a device ensuring tilting motions of the instrument insertion channel in accordance with an embodiment of the present invention.
Figure 9B:
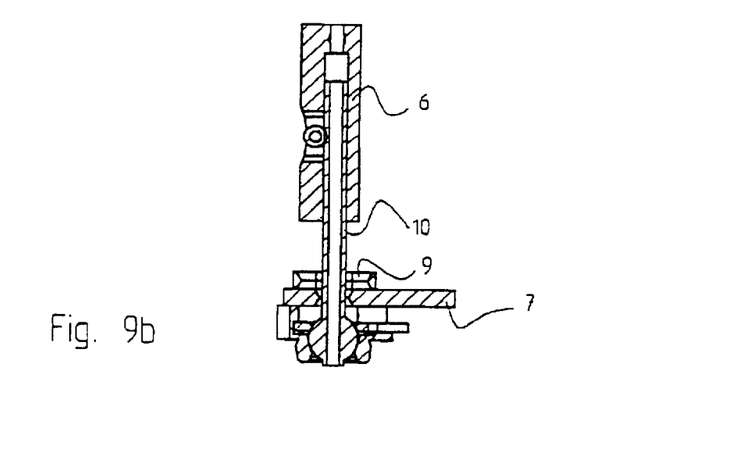
FIG. 9b shows a sectional image of an embodiment of a device ensuring tilting motions.

Through the instrument insertion channel 10, a tube can be inserted deep into the operation site, which will then serve as a channel for inserting further instruments as shown in FIG. 6, the advantage being a stabilization of the instruments inserted under navigation. The stabilization channel 23 then holds the inserted instruments. FIGS. 8 and 9 show a possibility where the instrument or the stabilization channel 23 can be cramped into a mounting 6, which is shifting in axial direction on the instrument insertion channel 10. Such mounting 6 can be lowered manually or automatically by a motor, electrically, hydraulically, by pneumatic power or by wire pull.

The orientation of the instrument insertion channel can be achieved by tilting. To allow this, two movable laminas 7 and 8, relative to the device 2 and shifting to each other (as shown in FIG. 9), are attached to the device. The instrument insertion channel 10 is guided through an oblong opening 9 in each lamina. By mechanical manual or automatic shifting of the laminas to each other, the instrument insertion channel is tiltable in various directions. Electrical, hydraulic or pneumatic actuations are possible for automatic shifting.

Figure 11:
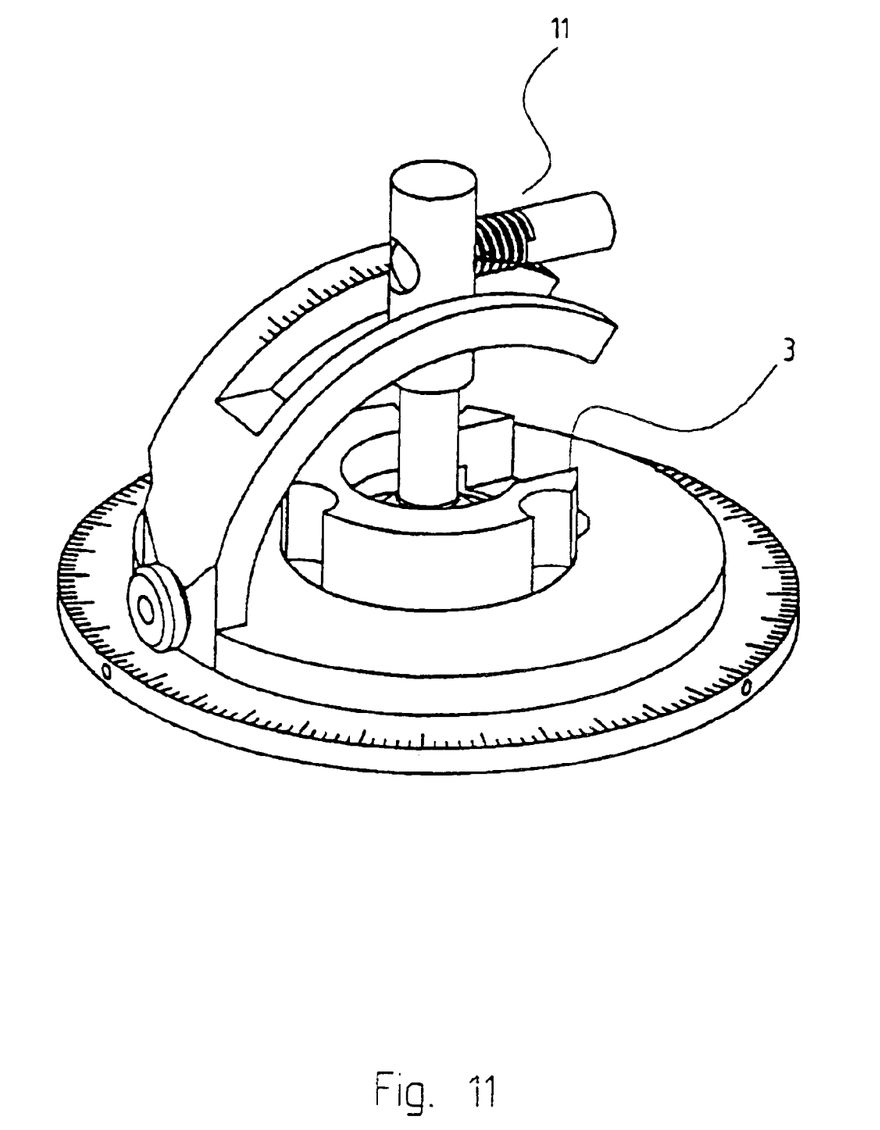
FIG. 11 shows a device with motor-powered adjustable instrument insertion channel in accordance with an embodiment of the present invention.

A further possibility of adjustment of the instrument insertion channel 10, as shown in FIG. 11, is to position the instrument insertion channel by means such as a rotating and tilting motion via a worm wheel 11 mechanically or by motor, pneumatically, or by wire pull.

The orientation of the instrument is directly readable by the scaling at the positioning unit. It could also be monitored via the above-mentioned markers in the MR image.

Figure 2:
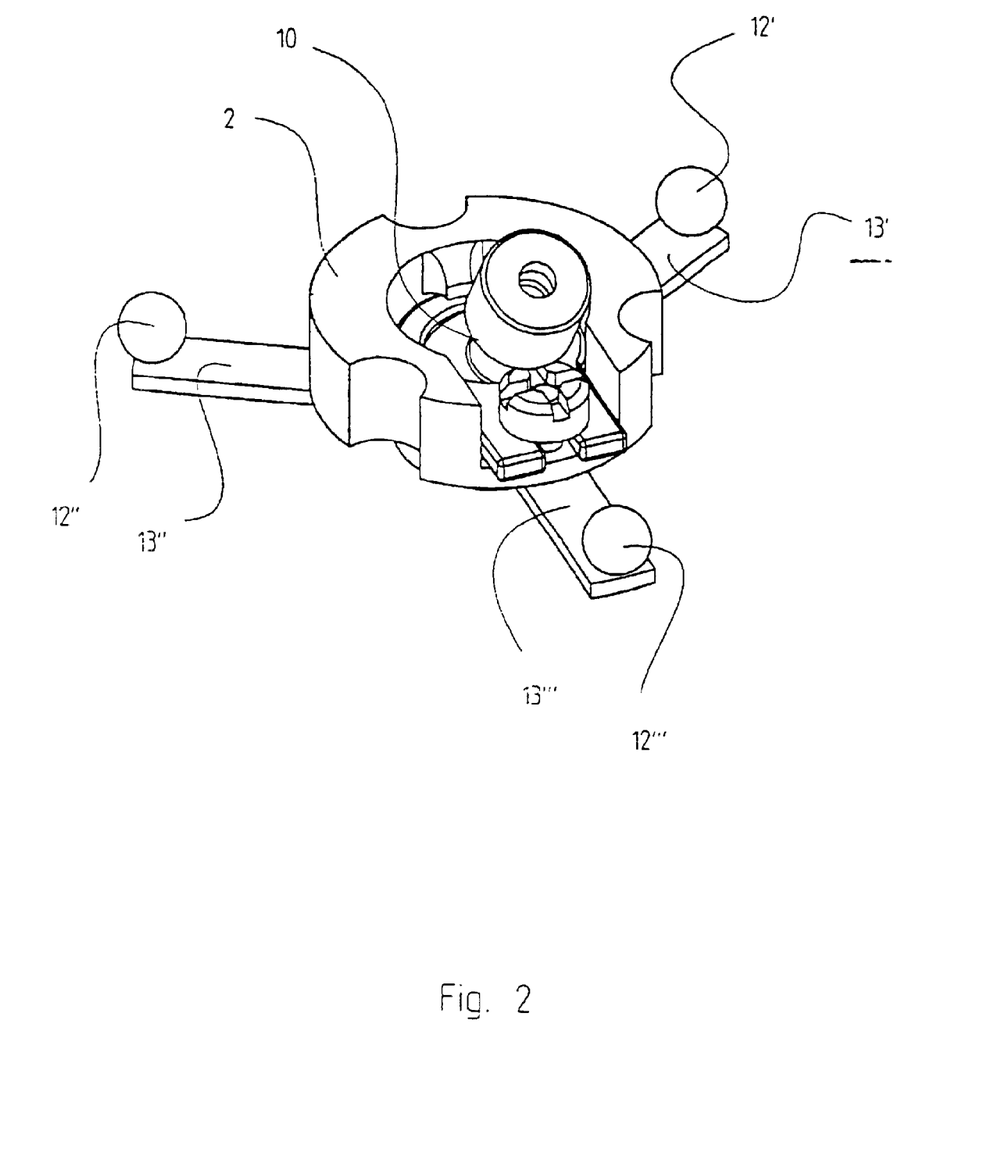
FIG. 2 shows navigation points at a device in accordance with an embodiment of the present invention.

In order to adapt the device to the imaging of the MRI device, a navigation system is to be integrated into the device itself. FIG. 2 shows a device 2 with an instrument insertion channel 10 and three laterally extended reflectors 12. The three mountings 13 for the reflectors 12 can be manufactured from one piece or can be three separate parts. The reflectors 12 could also be active optical light-emitting diodes. In such arrangement, the three reflectors or sending elements 12 can be monitored by an external camera system, and, due to the relative position of these three elements to each other, the spatial orientation of the device can be calculated and then be integrated in the MR image. Better still is the application of markers which are directly identified by the "magnet" (MRI), since this will prevent inaccuracies upon matching the coordination systems.

Figure 3:
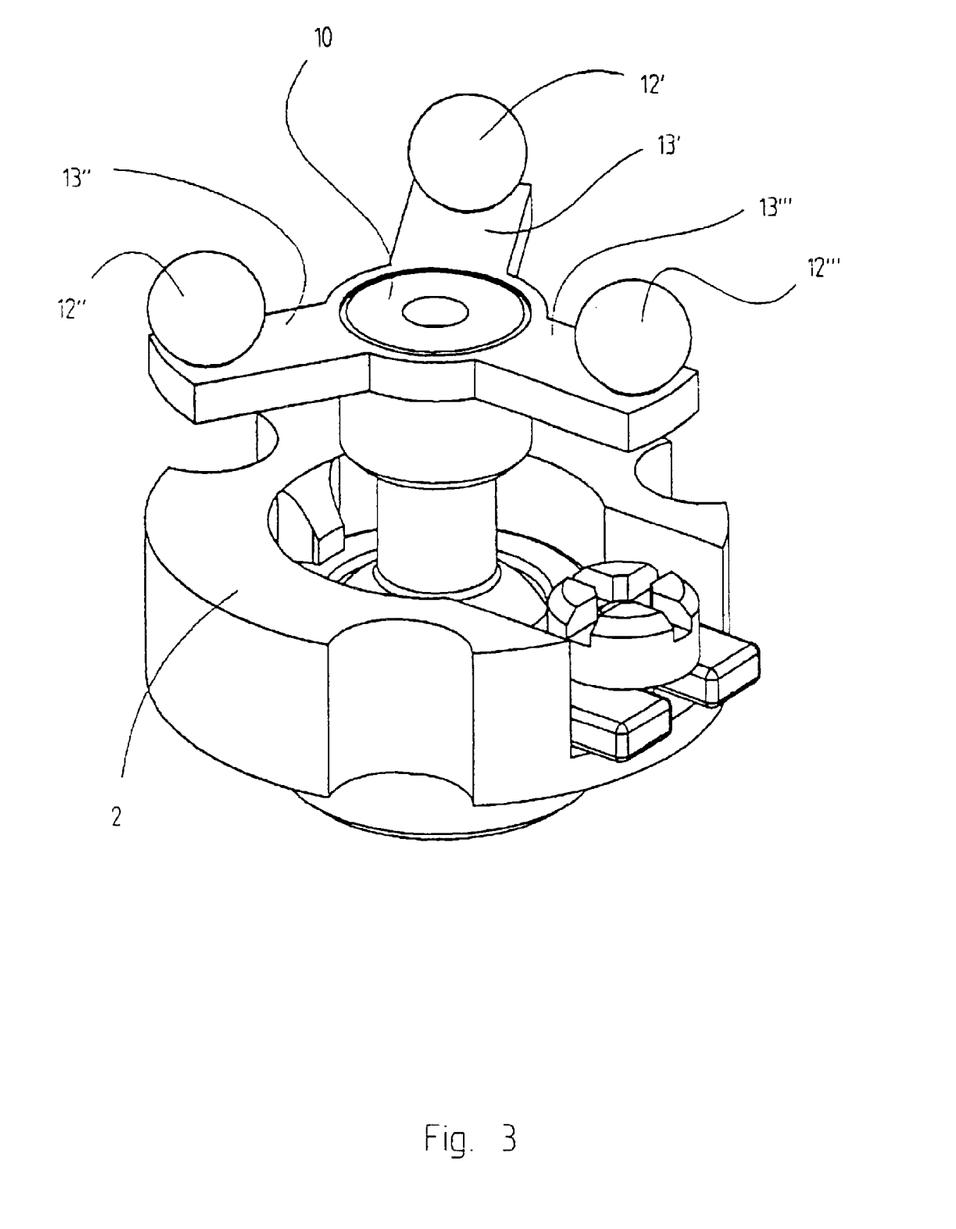
FIG. 3 shows navigation points at the instrument insertion channel of a device in accordance with an embodiment of the present invention.
Figure 10:
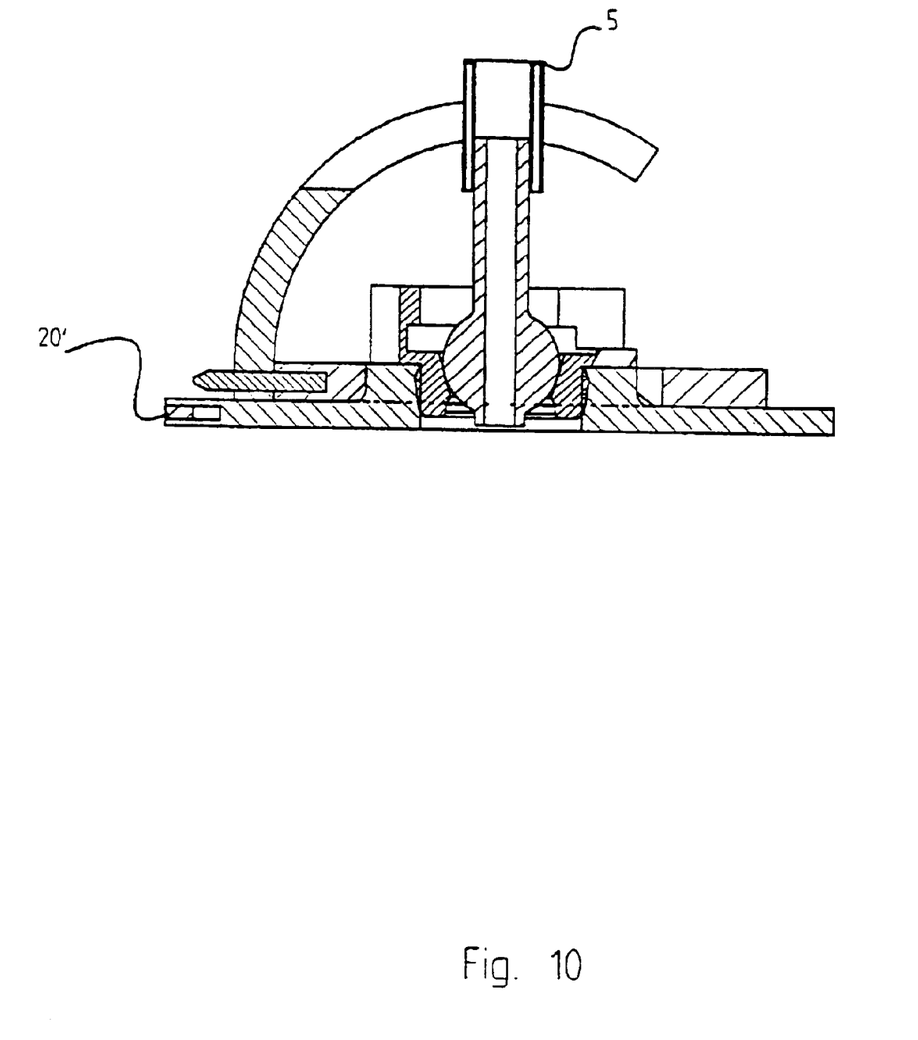
FIG. 10 shows a device with double-walled and contrast medium-filled top on the instrument insertion channel in accordance with an embodiment of the present invention.

FIG. 3 shows that this navigation device can also be directly connected to the instrument insertion channel 10. There could also be a navigation system for the device 2 a well as for the instrument insertion channel 10, resulting in having two navigation systems working with either different wavelengths or different codification or with different geometrically designed reflectors 12. The device can be manufactured of a material that is not depictable under MRI or with other radiological imaging methods. Single parts or areas of the device could be designed of a material that is actively or passively identifiable under MRI. For instance, the entire device for the operation under MRI could be manufactured of plastics such as PEEK, and only certain parts would be designed of titanium. The device could also be designed to have hollow spaces containing a liquid which will emit active signals, such as liquids with unpaired proton spin, for instance a gadolinium-based liquid. FIG. 10 shows a double-walled top filled with a signal-emitting liquid.

FIG. 5 shows a device 4 designed completely of plastics, preferably PEEK (polyetheretherketone). This device 4 is screwed into the skull with a self-cutting thread 19. Owing to the hardness of the plastic material, the device can be manufactured with a self-cutting thread. Such plastic device 4 is preferably designed as a disposable. Two navigation points, which could be placed inside the device either separated from one another or together, shall be exemplarily described at the device. As one possibility, the adjusting screw 17 in this PEEK instrument could be made of titanium. Titanium is imaged negatively, as a black spot, in the MRI device, so that the position of the device 4 is recognizable. With two further titanium points, the orientation of the device 4 can be identified in a similar way as with the navigation system of FIG. 3 or 2. A gadolinium-containing liquid is filled into a hollow space 18 in this device. This liquid is an active liquid for the MRI device, to be imaged as a white spot in the MR image. With three such hollow spaces filled with a gadolinium-containing liquid, here also the position of the device 4 can be determined. It is now possible to combine such active spots such as the hollow spaces 18 with the respective active or passive points 17, or self-reflecting or luminous marker points 12, which will be identified by the MRI device or a navigation system connected to the MRI device. In this way, the localization and navigation of the device within the MRI is ensured. By use of various positioning points depicted differently in the MR image, it is possible to achieve an exact allocation of the measured points to the points at the device.

A so-called TrackPointer, as described in patent specification 298 21 944.1, can also be connected to the device by implanting it in the instrument insertion channel 10.

Figure 7:
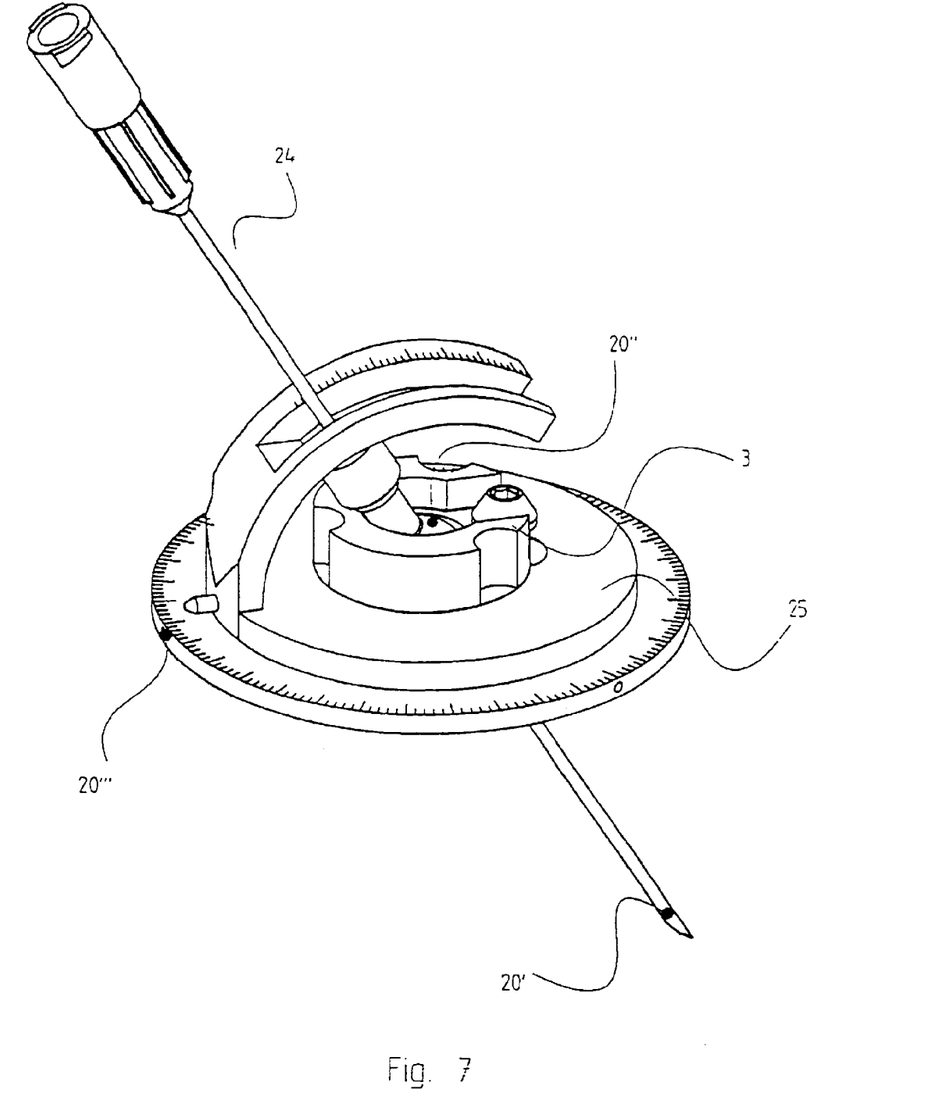
FIG. 7 shows attachment of MRI markers to the combination of device, instrument and angle measuring system in accordance with an embodiment of the present invention.

The orientation of the instrument with regard to the operation system, or, in other words, the adaptation of the image to the device presented herein via the MRI device, can also be realized with the markers, according to the principle 20 stated herein, not only attached to the device 3 itself, but also to the instrument 24, being inserted into the minimally-invasive channel 2 for a certain procedure, and to the angle measuring system 25 (FIG. 7).

FIG. 7 shows the process of pushing an instrument 24 through the device 3 into the operation area. A marker 20' is placed at its distal end 20', a second marker 20" in the insertion center of the device 3 as shown in FIG. 5. The third marker 20''' is positioned on the angle measuring system 25, which is freely adjustable around the device. The plane visible in the MR image will then be extended by the three points 20', 20", and 20'''. Thus one will always see the instrument with its inserted length in the brain region, which is determined by the third point placed on the circular angle measuring system 25. Such marking points could also be designed as small coils, as, for example, laid open with number 200 in patent application U.S. Pat. No. 5,353,795 by Sven P. Souza in FIG. 2. Such an element is an active coil sending with a certain frequency and being deflected according to the system presented in the above-mentioned patent.

Such a device can be used to insert probes, for mechanical and mechanical-surgical instruments or endoscopes. The instrument insertion channel 10 could also be designed in form of several lumens, resulting in several channels instead of only one. The device can also be used to insert larger instruments in open OP's. Such a device could be designed as either reusable or disposable instrument.

A system as presented herein can be used not only for surgical interventions and procedures, but also for the insertion of electrodes to fight Parkinson's disease. It could also be applied as a shunt.

REFERENCE NUMBERS

| | |
|---|---|
| 1. | Device |
| 2. | Device, general for adaptation to a navigation system |

-continued

| | |
|---|---|
| 3. | Device |
| 4. | Plastic Device |
| 5. | Double-walled top filled with contrast medium |
| 6. | Mounting |
| 7. | Movable lamina |
| 8. | Movable lamina |
| 9. | Opening |
| 10. | Instrument insertion channel |
| 11. | Worm wheel |
| 12. | Reflector/optically emitting elements |
| 13. | Reflector fitting |
| 14. | Angle adjustment azimuth angle |
| 15. | Angle adjustment zenith angle |
| 16. | Operation site |
| 17. | Titanium screw |
| 18. | Hollow space filled with gadolinium-containing liquid |
| 19. | Self-cutting thread |
| 20. | MRI markers according to one principle presented herein |
| 21. | Top with angle adjustment |
| 22. | Fixing screw |
| 23. | Stabilization channel |
| 24. | Instrument |
| 25. | Angle measuring system |

We claim:

1. An apparatus for inserting medical instruments into a human head, comprising:
a device configured to be fixedly positioned relative to a human skull, wherein the device configured to be fixedly positioned relative to a human skull is invisible under magnetic resonance imaging;
an instrument insertion channel movably connected to the device configured to be fixedly positioned relative to a human skull, wherein the instrument insertion channel is invisible under magnetic resonance imaging;
a means for determining the relative position of the instrument insertion channel with respect to the device configured to be fixedly positioned relative to a human skull such that once the position of the device configured to be fixedly positioned relative to a human skull is known the position of the instrument insertion channel is known;
at least three positioning markers fixedly positioned with respect to the device configured to be fixedly positioned relative to a human skull, wherein the positioning markers can be distinguished from one another by magnetic resonance imaging, wherein the position of the device configured to be fixedly positioned relative to a human skull can be determined by monitoring the at least three positioning markers under magnetic resonance imaging such that the position of the instrument insertion channel can be determined via the means for determining the relative position of the instrument insertion channel with respect to the device configured to be fixedly positioned relative to a human skull; and
a means for showing a virtual image of the instrument insertion channel in a magnetic resonance image of the human head.

2. The apparatus according to claim 1, wherein at least one of the at least three positioning markers comprises a coil.

3. The apparatus according to claim 1, wherein at least one of the at least three positioning markers comprises a volume filled with a material positively or negatively identifiable under magnetic resonance imaging.

4. The apparatus according to claim 1, wherein one of the at least three positioning markers comprises a titanium screw.

5. The apparatus according to claim 1, wherein at least one of the at least three positioning markers are within the device configured to be fixedly positioned relative to a human skull.

6. The apparatus according to claim 1, further comprising at least three additional positioning markers fixedly positioned with respect to the instrument insertion channel,
wherein the means for determining the relative position of the instrument insertion channel with respect to the device configured to be fixedly positioned relative to a human skull comprises:
the at least three positioning markers fixedly positioned with respect to the device configured to be fixedly positioned relative to a human skull, and
the at least three additional positioning markers fixedly positioned with respect to the instrument insertion channel.

7. The apparatus according to claim 6, wherein at least one of the least three additional positioning markers fixedly positioned with respect to the instrument insertion channel comprises a coil.

8. The apparatus according to claim 6, wherein the at least three additional positioning markers fixedly positioned with respect to the instrument insertion channel comprise optically active or optionally reflecting positioning markers.

9. The apparatus according to claim 7, wherein the at least three positioning markers fixedly positioned with respect to the device configured to be fixedly positioned relative to a human skull are distinguishable from the at least three additional positining markers fixedly positioned with respect to the instrument insertion channel correspond to a different codification.

10. The apparatus to claim 9, wherein the at least three positioning markers fixedly positioned with respect to the device configured to be fixedly positioned relative to a human skull and the at least three additional positioning markers fixedly positioned with respect to the instrument insertion channel correspond to a different codification.

11. The apparatus according to claim 1, wherein the means for determining the relative position of the instrument insertion channel with respect to the device configured to be fixedly positioned relative to a human skull comprises:
a means for measuring an azimath angle that the instrument insertion channel makes with respect to an axis parallel to a plane of the element, and
a means for measuring a zenith angle that the instrument insertion channel makes with respect to the plane of the element.

12. The apparatus according to claim 11, wherein the means for measuring the azimuth angle comprises a sealing on a top piece attached to the element, and
wherein the means for measuring the zenith angle comprises a scaling on the element.

* * * * *

UNITED STATES PATENT AND TRADEMARK OFFICE
CERTIFICATE OF CORRECTION

PATENT NO. : 6,989,015 B2
DATED : January 24, 2006
INVENTOR(S) : Wolfgang Daum and Axel Winkel It is certified that error appears in the above-identified patent and that said Letters Patent is hereby corrected as shown below:

Column 2,
Line 45, "zenith angle 1" should read -- zenith angle 15 --.

Column 2,
Lines 54 and 55, "markers according to the principles 20', 20", and 20'" stated herein" should read -- markers 20', 20", and 20'" according to the principles stated herein --.

Column 4,
Line 35, "placed at its distal end 20', a second marker" should read -- placed at its distal end, a second marker --.

Column 6,
Line 32, "or optionally reflecting" should read -- or optically reflecting --.
Line 37, "additional positining markers" should read -- additional positioning markers --.
Lines 38 and 39, "instrument insertion channel correspond to a different codification." should read -- instrument insertion channel --.
Line 50, "measuring an azimath angle" should read -- measuring an azimuth angle --.
Line 57, "comprises a sealing on a top piece" should read -- comprises a scaling on a top piece --.

Signed and Sealed this

Eighteenth Day of April, 2006

JON W. DUDAS
*Director of the United States Patent and Trademark Office*